(12) United States Patent
Fischer

(10) Patent No.: US 7,540,612 B2
(45) Date of Patent: Jun. 2, 2009

(54) DEVICE AND METHOD FOR DETERMINING THE HEIGHT OF THE MIDDLE OF THE PUPIL IN RELATION TO THE LOWEST PART OF A PAIR OF EYEGLASSES

(76) Inventor: Eric Fischer, St. Rita Weg 15, Oberhaching (DE) 82041

( * ) Notice: Subject to any disclaimer, the term of this patent is extended or adjusted under 35 U.S.C. 154(b) by 269 days.

(21) Appl. No.: 11/210,450

(22) Filed: Aug. 25, 2005

(65) Prior Publication Data

US 2006/0077342 A1  Apr. 13, 2006

(30) Foreign Application Priority Data

Oct. 9, 2004  (EP) .................................. 04021588

(51) Int. Cl.
*A61B 3/10* (2006.01)
*A61B 3/14* (2006.01)
*A61B 3/04* (2006.01)

(52) U.S. Cl. ........................ 351/204; 351/208; 351/231

(58) Field of Classification Search ................. 351/204, 351/205, 208, 211, 218, 221, 222, 223, 231
See application file for complete search history.

(56) References Cited

U.S. PATENT DOCUMENTS

| 4,505,043 | A |   | 3/1985 | Sztuka ........................ 33/174 |
| 5,640,775 | A | * | 6/1997 | Marshall ........................ 33/28 |

* cited by examiner

*Primary Examiner*—Ricky L Mack
*Assistant Examiner*—Brandi N Thomas
(74) *Attorney, Agent, or Firm*—LaMorte & Associates

(57) ABSTRACT

A measurement instrument and its associated method of use to record a pupil center position of a person's eye. The instrument has a chassis and a free swinging assembly that is pivotably attached to the chassis. The swinging assembly has alignment points that remain in a horizontal plane as the swinging assembly swings. The instrument is attached to a set of eyeglass that are worn on that person's head. While wearing the measuring instrument, a person is made to assume a natural head position for a specific activity. Once a natural head position is found, the swinging assembly is set into a locked position. The pupil center point can then be determined by observing the now locked alignment points from a predetermined vantage point.

14 Claims, 5 Drawing Sheets

DEVICE AND METHOD FOR DETERMINING THE HEIGHT OF THE MIDDLE OF THE PUPIL IN RELATION TO THE LOWEST PART OF A PAIR OF EYEGLASSES

RELATED APPLICATIONS

This Application claims priority of co-pending European Patent Application No. 04021588.1, filed Sep. 10, 2004.

BACKGROUND OF THE INVENTION

1. Field of the Invention

In general, the present invention relates to measurement devices used to properly fit eyeglasses. More particularly, the present invention relates to instruments used to determine the center of an eye's pupil for use in fabricating multi-focal lenses.

2. Prior Art Description

Eyeglasses can be either framed or frameless. Framed eyeglasses have lenses that are mounted on a frame made, for example, from an aluminum or titanium alloy or some other material. Frameless glasses have lenses that are only secured by a nosepiece and the ear handles of the eyeglasses.

Eyeglasses can also have either single-focal lenses or multi-focal lenses, so-called progressive lenses or multi-focal lenses. When the wearer is at the opticians buying a new pair of such eyeglasses, certain centering data has to be recorded in order to fit the new lenses. This data is necessary for the grinding of the lenses and for when they are fitted onto their frames, even in the case of frameless glasses. In order to ensure that the multi-focal lenses correspond to the wearer's individual requirements, the manufacturers of such multi-focal lenses need to know a point on the lens directly in front of the pupil when the wearer is looking straight ahead and is said to have a natural posture and head position. When it comes to measuring the height of the middle of the pupil in relation to the lowest part of the spectacle frame, or in the case of frameless glasses in relation to the lowest part of the lens, the normal approach is that the optician will stand in front of the wearer and ask him or her to look straight ahead. At the same time, the wearer will be requested to take on a natural posture and head position. The optician will then try to sight the middle of the pupil and mark it on the lens using a felt marker. In the case of a new pair of spectacles, an optician will mark the demo glass.

There are a number of disadvantages of this conventional approach. If the wearer were to take on a posture and head position that is different to his natural one, a wrong measurement can be recorded. For example, if the wearer tilts his head further back than normal, this causes him to look through a lower part of the lens in relation to the lowest part of the eyeglasses. The optician would then incorrectly sight the position of the middle of the pupil because of the wearer's unnatural posture and head position. If the lenses of the eyeglasses are made using this incorrect measurement, the eyeglasses would be incorrect.

It has been observed that a person often holds his/her head in an unnatural position when being fitted for eyeglasses. When the optician stands in front of a person to take a pupil measurement, that person often assumes a posture and head position that is different to his natural one. For example, a person may stand far more erect that he normally would. Alternatively, a person may tilt his head further back than normal. The incorrect measurements may render the manufactured eyeglasses unusable, with the result that the optician has to redo the measurements and replace the lenses.

Another problem resulting from this conventional approach is that in order to mark the spectacle lens, or the demo glass, the optician has to have the same eye height as the customer in order to avoid the problem of vertical parallax. This, in turn, is only possible if the optician himself, or a member of his staff, is of the same height as his customer. Since this is not usually the case, the customer is asked to sit down so that the person taking the measurements can sit opposite the customer and simulates the same height. Even if, when seated as described, the person taking the measurements is of the opinion that they are at the same eye height as the wearer, this is still subjective, because there is no proof whatsoever that the eye height of the wearer is the same as the eye height of the person taking the measurement. Relevant observations have shown that a difference in eye height, i.e. in the height of the middle of the pupil, of some 5 cm is typical, thus leading to the above mentioned problem of vertical parallax. This means that the inaccuracy with which the distance between the middle of the pupil and the lowest part of the eyeglasses is measured is some 1.1 mm while an accuracy of +/−0.2 mm is required.

In the prior art, measurement devices have been developed that are used in the proper fitting of eyeglasses with multi-focal lenses. For instance U.S. Pat. No. 4,505,043 to Sztuka, entitled Height Measurement Gage For Multifocal Lenses, a measurement device is shown that attaches to the frame of a pair of eyeglasses. The device records the position of the pupil relative the eyeglass frame. This eliminates the need to mark the lens with a felt marker. However, the device is only suitable with eyeglasses having specific angles of inclination. Furthermore, the device does not eliminate errors caused by taking measurements while a person's head is in an unnatural position.

U.S. Pat. No. 5,640,775 to Marshall, entitled Determining And Marking Apparatus And Method For Use In Optometry And Ophthalmology, discloses a measuring device where a person positions a light between his/her eye and a distant target. The light theoretically shows the person's line of sight. The point where the light passes through the eyeglass lens is marked and used in the making of the multi-focal lenses.

The holding of a light source in front of the eye is an odd act that causes people to cock, tilt, and otherwise hold their head in an unnatural position as they attempt to align the light and a distant target. Consequently, the device of the Marshall patent does not provide a system that creates a measurement while a person is holding his/her head in a natural position and posture.

A need therefore exists for a device that can be used to accurately measure the position of a person's pupil in relation to a pair of eyeglasses, without having a person move his/her head from a natural position and posture. This need is met by the present invention as described and claimed below.

SUMMARY OF THE INVENTION

The present invention is a measurement instrument and its associated method of use. The measurement instrument is used to record a pupil center position of a person's eye.

The instrument has a chassis and a free swinging assembly that is pivotably attached to the chassis. The swinging assembly has alignment points that remain in a horizontal plane as the swinging assembly swings. The instrument is attached to a set of eyeglass that are worn on that person's head. As a result, the instrument moves with the person's head and is effected by head position and posture.

While wearing the measuring instrument, a person is made to assume a natural head position for a specific activity. Once a natural head position is found, the swinging assembly is set into a locked position. Once in the locked position, the orientation between the alignment points and the chassis is set. The pupil center point can then be determined by observing the alignment points from a predetermined vantage point.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Figure 1:
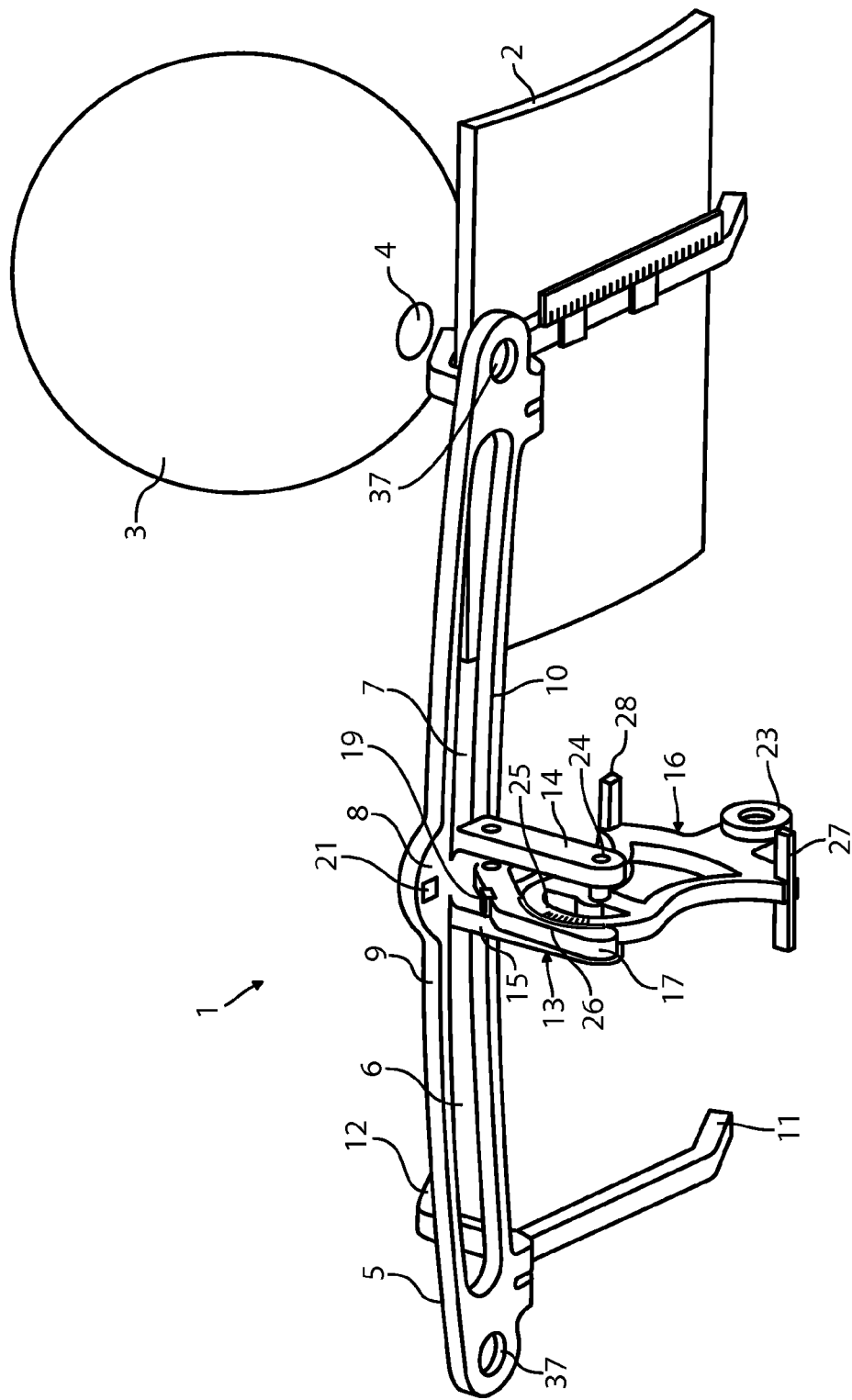
FIG. 1 is a perspective view of an exemplary embodiment of the present invention measurement instrument, shown in conjunction with a lens and a human eye.
Figure 2:
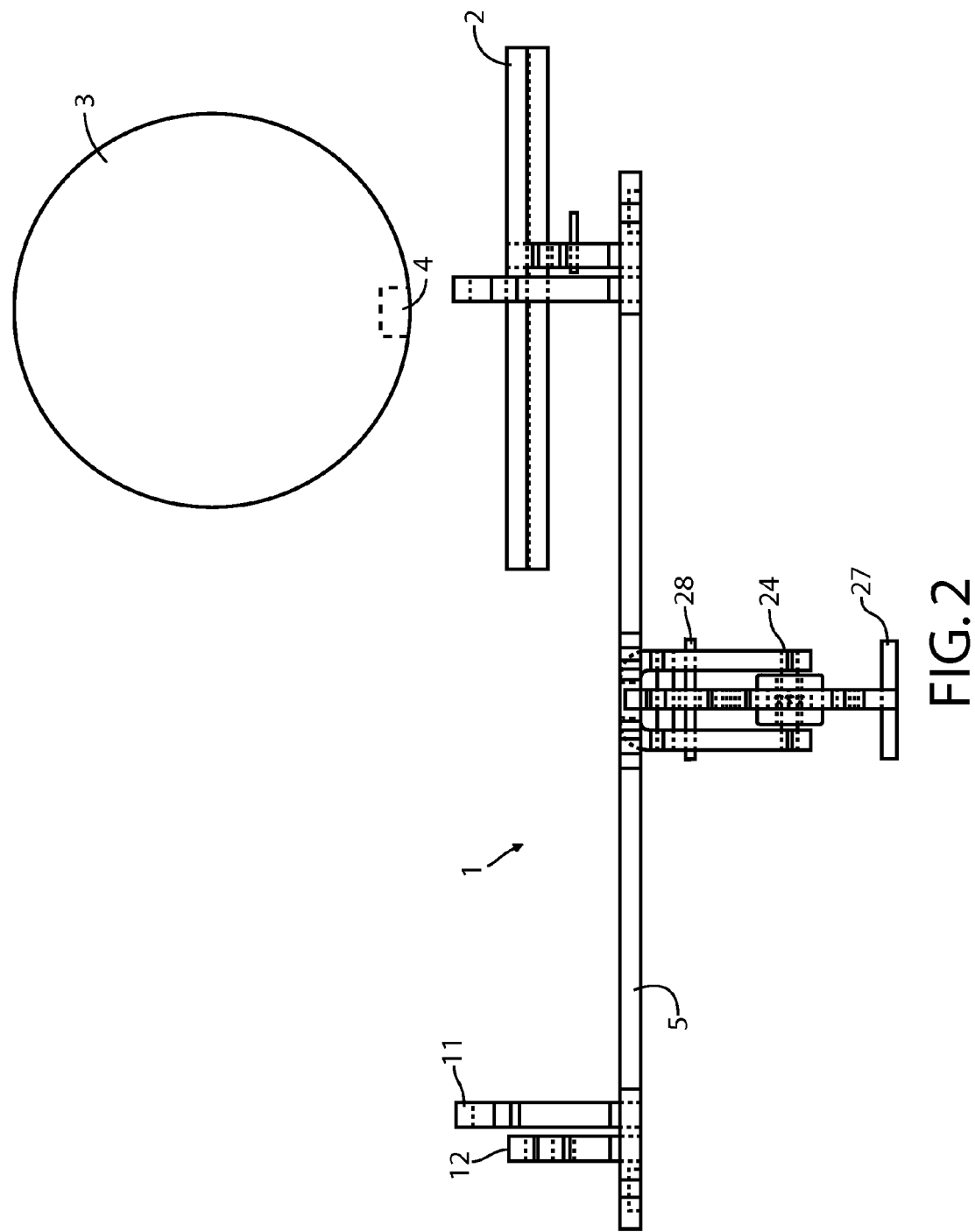
FIG. 2 is a top view of the embodiment of FIG. 1.
Figure 3:
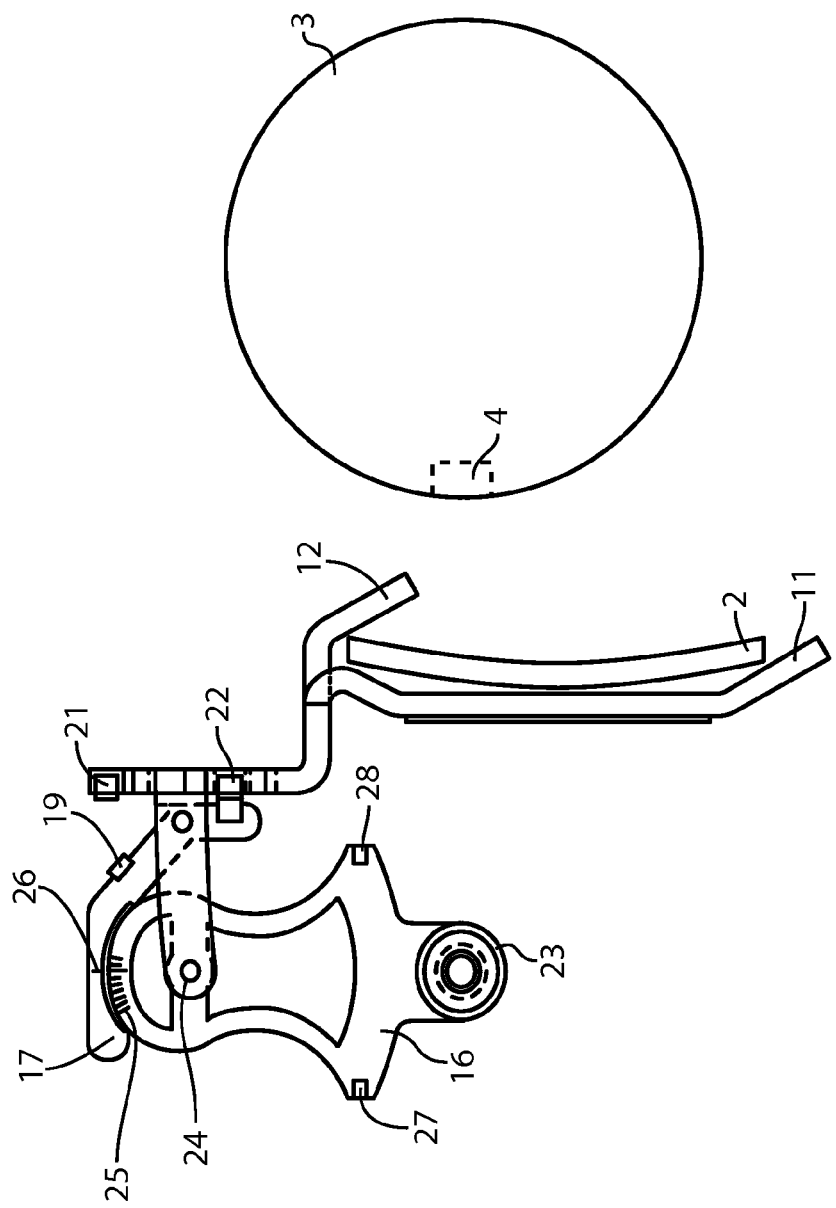
FIG. 3 is a side view of the embodiment of FIG. 1.

FIG. 1, FIG. 2 and FIG. 3 show an exemplary version of a measurement instrument 1, in accordance with the present invention. The measurement instrument 1 is shown in conjunction with schematic lens which is to be measured in relation to the pupil of a person's eye. Reference number 2 refers to the schematic lens. Reference number 3 refers to a schematically represented eye of the wearer and reference number 4 refers to the pupil.

As is shown from the drawings, measurement instrument 1 exhibits a chassis 5, which has an overall long stretched-out circular-arc shaped configuration. So as to save on weight, the chassis 5 can, for instance, be made of an aluminum alloy or of plastic materials and has two cut-outs 6,7, which also serve the purpose of saving on weight. In the area between the two cut-outs 6, 7, the chassis 5 exhibits a plinth 8 which connects the over-bar 9 with the under-bar 10 of the chassis 5. In the area of the two distal ends of the chassis 5, two stays 11, 12 are present that form an inverted V-shape. The two stays 11, 12 include various angles so that they attach and support the measurement instrument 1 on the top of the eyeglass frames or lenses 2.

Using stays 11, 12, the measurement instrument 1 is attached to the lens 2 or the frame surrounding the lens 2, depending upon whether the eyeglasses are frameless or framed. The frame of the eyeglasses or the lenses 2 can be held between the stays 11, 12 at both distal ends of the measurement instrument 1 and in such a way that the measurement instrument 1 on the frame or, in the case of frameless spectacles, resting on the top of the two lenses, will not slip off.

The plinth 8 of the chassis 5 supports a fork assembly 13 that points from the chassis 5 at a right angle towards the front. The two forked arms 14, 15 create a space between them, the purpose of which is to hold a weighted swing assembly 16.

The weighted swing assembly 16 is shown in the locked position, brought about by a brake-arm 17, which pivots horizontally on a brake arm pin 18 and rest on the radius of the swing assembly 16. See the view from above of FIG. 3.

On the side facing the plinth 8 and the chassis 5, the brake arm 17 holds small permanent magnets 19, 20. The small permanent magnets 19, 20 selectively connect to permanent magnets 21, 22 that are on the plinth 8. Depending upon the position of the brake-arm 17, the brake arm 17 can be moved into the locked position shown in the figures. Alternatively, the brake arm can be moved into free position when the magnetic material 19 is brought into contact with the permanent magnet 21. In the free position, the brake-arm 17 is released from the locked position, in which it is in contact with the swing assembly 16, via a swing assembly weight 23. The weighted swing assembly 16 pivots on a transverse horizontal axel 24.

As is best shown in FIG. 3, the swing assembly 16 exhibits a degree scale 25 on the side facing the brake arm 17. The degree scale 25 enables the angle of inclination of the spectacle frame or lenses 2 can be recorded from a mark 26 envisaged on the brake-arm 17.

On the swing assembly 16 there are two alignment pins 27, 28, whose cross-section is rectangular and which have been given a predetermined longitudinal extension. The alignment pin 28 that is closer to the chassis 5 is higher than the pin 27 that is further away from the chassis 5.

Figure 4:
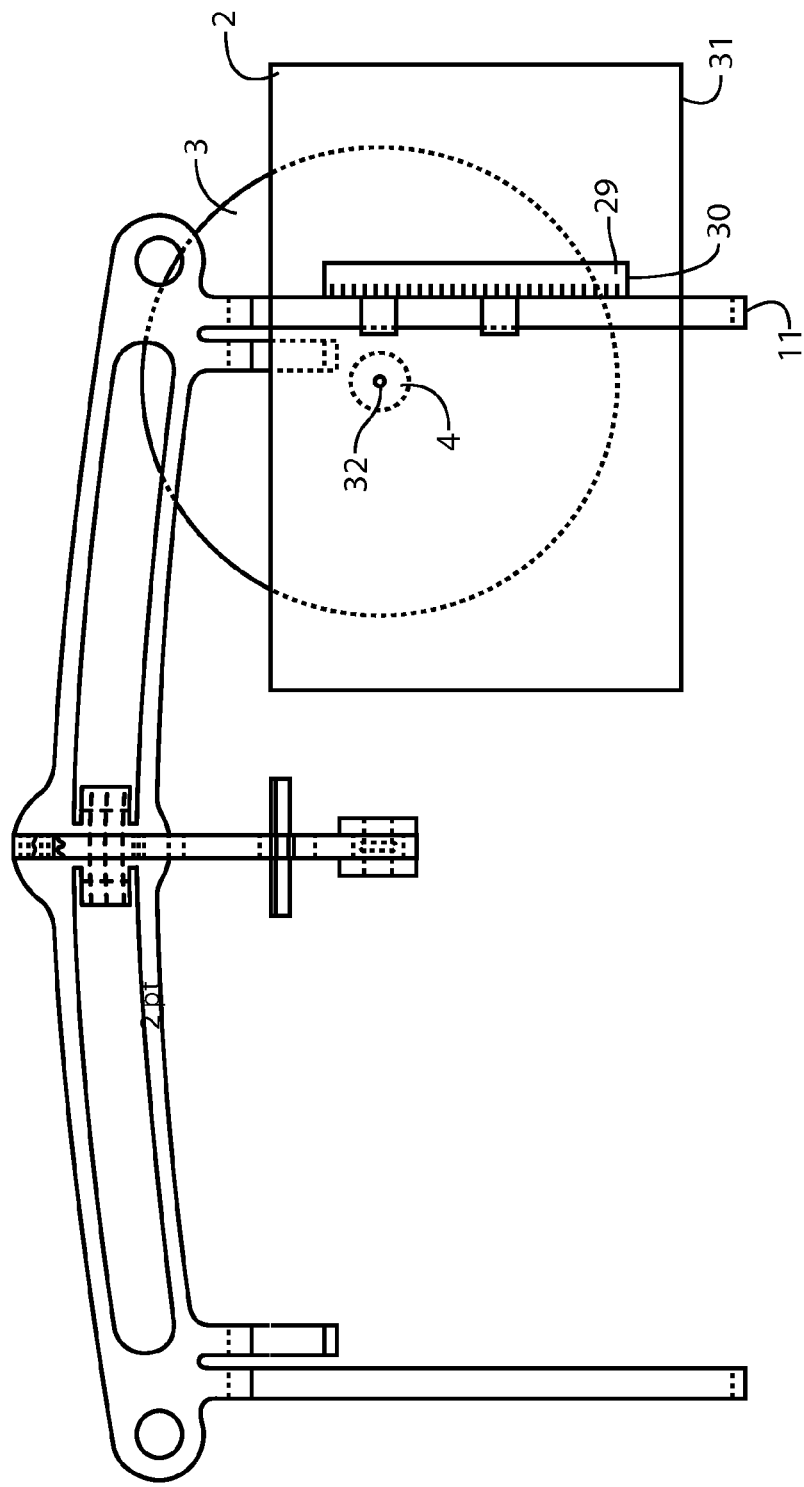
FIG. 4 is a front view of the embodiment of FIG. 1.

Referring to FIG. 4, it can be seen that a sliding measurement scale 29 is present on the lengthwise axial of the stay 11. The sliding measurement scale 29 can be shifted on the stay 11 so that the zero point 30 of the measurement scale 29 can be brought into line with the lower rim 31 of the lens 2. Once positioned, the distance between the lower rim 31 and the pupil center 32 of the pupil 4 can be directly read off the measurement scale 29.

Referring to FIGS. 1-4 in unison, it will be understood that to measure the distance between the lower rim 31 of the lens 2 and the pupil center 32, the instrument 1 is placed on the eyeglasses using stays 11, 12. The position of the brake-arm 17 is such that it is free to move having been released from its locked position in contact with the swing assembly 16 by flipping it up so that the two magnets 20, 22 are no longer in contact. In this free position, the brake-arm 17 is held by means of the magnetic material 19 and the permanent magnet 21 on the chassis 5 and the plinth 8. The customer wearing the eyeglasses and the instrument 1 is asked to assume a natural posture and head position and, in so doing, to focus on a point in the distance. The customer can do this standing in the shop, walking round the shop or looking at different points in the distance so that he assumes his own specific natural posture and head position which he will also assume when, at a later date, he wears the eyeglasses that are about to be custom-made for him.

In addition to the above mentioned alternatives, the wearer can also assume a different position. A wearer can, for instance, sit in a car, at a desk or in front of a computer screen so that with the help of the measurement instrument 1 it is possible to produce eyeglasses for a specific use that relate to the posture and head position assumed by the wearer when carrying out the specific activity.

The swing assembly 16 does not actually follow the movements of the head, and the body of the wearer, but rather pivots on the axel 24 in relation to the chassis 5. The fictive horizontal plane created by the alignment pins 27, 28 therefore corresponds to the wearer's horizontal line of sight. The wearer's horizontal line of sight is specific to the wearing and depends upon the position and activity of the wearer. A wearer may therefore have different lines of sight when driving and when walking.

Since, while the wearer's horizontal line of sight is being recorded, the customer is not being disturbed by, for instance, the optician standing in front of him. Rather, the wearer assumes a natural posture and head position so that the horizontal plane created by the alignment pins 27,28 correspond to the wearer's specific horizontal line of sight.

The wearer's natural posture and head position can be determined by the optician, or a member of his staff and, for instance, assessed while talking to the wearer in the shop. Once a natural posture and head position is observed, the optician, or a member of his staff, can release the brake arm 17 and record the measurement. The brake arm 17 is preferably released from the side, or from behind, so that the wearer is not disturbed in any way and continues to assume his natural posture and head position. Once the brake arm 17 is released, the permanent magnet 20 comes into contact with permanent magnet 22 and the horizontal line of sight specific to the wearer is captured and recorded by means of the contact between the brake-arm 17 and the horizontal swing assembly 16.

The height of the pupil center 32 in relation to the lower rim 31 of the lens 2 is then calculated on the basis of the wearer's horizontal line of sight as determined above. For this purpose, the optician, or a member of his staff, can ask the wearer to sit down and then take up a position sitting opposite him at a distance of about 60 cm. Doing this will not change the wearer's recorded horizontal line of sight because contact exists between the brake-arm 17 and the swing assembly 16 prevents the swing assembly 16 from moving out of its locked position.

Figure 5:
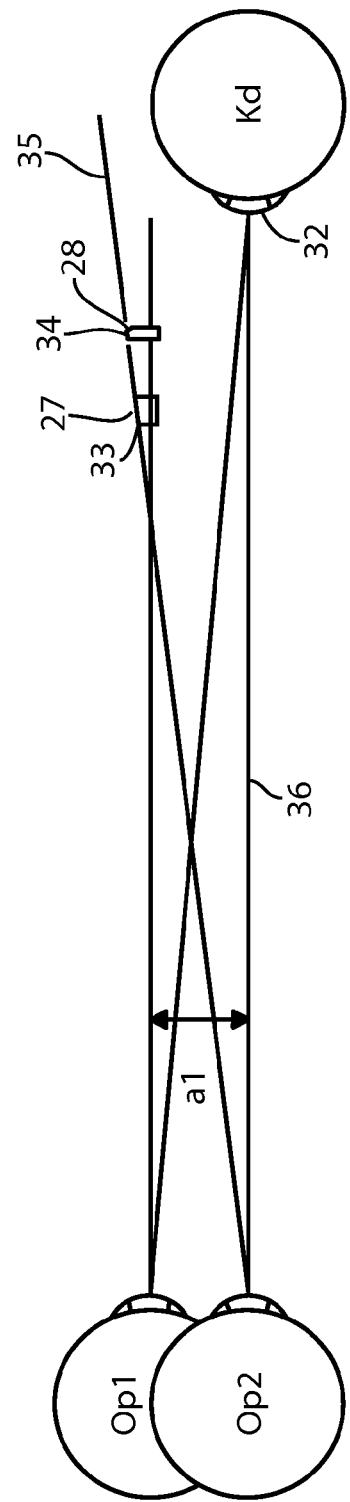
FIG. 5 is schematic diagram depicting the manner in which part of the measuring instrument operates.

Referring to FIG. 5, it can be seen that the customer Kd sits opposite the optician Op1, or a member of his staff, at a distance of about 60 cm. The optician Op 1 lines up the back alignment pin 28 and the front alignment pin 28 so that they optically cover each other and can then make a mark. The mark can be made using a felt marker on the lens 2. The mark reflects the position of the pupil center of the customer Kd, whereby during this process the customer Kd is looking directly into the center of the optician's eye.

The accuracy called for by the manufacturers of multi-focal lenses with respect to the height of the pupil center in relation to the lower rim of the lens or of the spectacle frame is thus possible. However, as is clear from FIG. 5 of the drawing, the alignment pins 27, 28 are not at exactly the same height as the center of the pupil 32 but rather slightly above. Despite this distance, the level of accuracy demanded by the manufacturers of multi-focal lenses can already be attained with the measurement instrument 1 in accordance with the invention at issue.

In the case of the version shown in the drawing, the cross section of the alignment pins 27,28 is rectangular whereby the back alignment pin 28 is some 0.175 mm higher than the front alignment pin 27. This enables the optician to create an Op2 line of sight with the help of the front top visible edge 33 of the front alignment pin 27 and the front top visible edge 34 of the back alignment pin 28. This Op2 line of sight intersects with the horizontal line of sight 36, which corresponds to the wearer's horizontal line of sight at a distance of some 60 cm from lens 2 with the pupil center of the optician so that the pupil center Op 2 of the optician is at exactly the same height as the center of the pupil 32 of the customer Kd. The measurement instrument 1 in accordance with the invention at issue makes it possible to determine the height of the pupil center in relation to the lowest point of the eyeglasses in a reproducible manner with the wearer assuming a natural posture and head position. In addition, the problem of vertical parallax caused by wearers and opticians having different eye heights is also avoided.

With the help of two reference points 37 envisaged on the chassis, which have been positioned at a predetermined distance from each other at the distal ends of the chassis a reference scale has been created with which, using electronic image processing, the distance between the lower rim 31 and the pupil center 32 can be calculated on the basis of an image of the customer wearing the spectacle frame and the instrument. For this purpose, on the arms 14, 15 reference points 38 are envisaged which are positioned at a predetermined distance from the reference points 37 and with the help of whose relative positions in relation to reference points 37, it can be determined whether the image was taken from the front or at an angle to the vertical plane.

Referring back to FIGS. 1-3, it can be seen to utilize the measurement instrument 1, the measurement instrument 1 is attached to a pair of eyeglasses. The eyeglasses are then worn by a person. As the measurement instrument 1 is being worn, the weighted swing assembly 16 pivots freely on the horizontal rotational axis such that a horizontal plane created by means of two alignment pins 27, 28 mounted on the swing assembly 16 always runs parallel to the wearer's horizontal line of sight even when the wearer changes his posture or head position. In other words, with the help of the freely pivoting swing assembly 16 or, to be more precise, with the help of the two alignment pins 27, 28 mounted on it, a horizontal plane is created which follows the wearer's horizontal line of sight as he assumes different posture and head positions.

The horizontal plane that is created follows the horizontal line of sight of the wearer. When, for example, the wearer walks around having assumed a posture and head position that is comfortable and therefore natural for him when looking into the distance, the horizontal plane created by the alignment planes always runs parallel to the horizontal line of sight of the wearer, whereby the distance between the parallels can be zero. This means that at any one time the horizontal plane created by the two alignment pins 27, 28 is always in the same plane as the wearer's horizontal line of sight. Due to the fact that the swing assembly 16 to be locked in the position when the wearer has assumed his natural posture and head position, the horizontal plane created by the alignment pins 27, 28 can be captured and recorded.

Once the wearer's horizontal line of sight has been captured and recorded, the wearer's horizontal line of sight no longer changes. To align the optician's pupil center with the wearer's horizontal line of sight, the alignment pins 27, 28 can be marked with contrasting colors. From the opticians point of view looking towards the wearer, the alignment pin 27 that is closer and behind can have a different color to the pin that is closer to the optician. So that the optician can be sure he, for instance, stands or sits opposite the wearer and adjusts his standing or sitting height until the differently colored pin 27 that is further back has been completely covered by the pin 28 that is further forward. This is the point at which the center of the pupil of the wearer is on the same plane as the center of the pupil of the optician.

At this point the optician can, for instance with a felt marker, physically mark (in color) the point on the lens or on the demo glass at exactly the height of the center of the pupil of the wearer. Using a simple measuring instrument in the form of a ruler or some such device the optician can then measure the distance between the lower rim of the spectacle frame or the lens and the center of the pupil.

It will be understood that the embodiment of the present invention measurement instrument that is illustrated is merely exemplary and that many features of the instrument can be redesigned in manners that are functionally equivalent. All such variations, modifications and alternate embodiments are intended to be included within the scope of the present invention as claimed.

What is claimed is:

1. A measurement instrument for recording the height of a pupil center of a person in relation to a point on a set of eyeglasses being worn by that person, said measurement instrument comprising:
   a chassis that selectively attaches to said eyeglasses;
   a swing assembly pivotably coupled to said chassis at a single pivot point that enables said swing assembly to swing freely in a single vertical plane;
   at least two alignment pins supported by said swing assembly, wherein said alignment pins are straight, parallel and spaced apart, and wherein gravity causes said alignment pins remain aligned in a horizontal plane as said swing assembly pivots freely in said vertical plane;
   a locking mechanism for selectively locking said swing assembly in a locked position relative said chassis, thereby locking said at least two alignment pins in a set angle of inclination relative said chassis.

2. The measurement instrument according to claim 1, further including a measurement scale disposed between said chassis and said swing assembly for visually determining said angle of inclination of said at least two alignment pins.

3. The measurement instrument according to claim 1, wherein said alignment pins are colored in contrast.

4. The measurement instrument according to claim 1, wherein said alignment pins are spaced and sized to align with the pupil center of the person when viewed in a horizontal plane at a predetermined distance.

5. A method of recording a pupil center position of a person's eye, said method comprising the steps of:
   providing an instrument that has a chassis and a free swinging assembly that is pivotably attached to said chassis at a single point, wherein said swinging assembly swings only in a vertical plane has alignment points that remain in a horizontal plane as said swinging assembly swings;
   attaching said instrument to a person's head so that said instrument moves with the person's head;
   having the person assume a natural head position for a specific activity;
   providing a break arm on said chassis that can selectively contact said swinging assembly, therein locking said swinging assembly into a locked position when said head is in said natural head position; and
   determining the pupil center point of the person by observing said alignment points while in said locked position.

6. The method according to claim 5, wherein said step of attaching said instrument to a person's head includes providing eyeglasses, placing said eyeglasses on a person's head and attaching said instrument to said eyeglasses.

7. The method according to claim 5, wherein said step of determining the pupil center point of the person includes aligning said alignment points with the pupil center point at a predetermined point of observation, thereby creating an imaginary observance line from said point of observation to said pupil center point that touches said alignment points.

8. The method according to claim 7, wherein said step of attaching said instrument to a person's head includes providing eyeglasses, placing said eyeglasses on a person's head and attaching said instrument to said eyeglasses, wherein said eyeglasses has a lens element positioned in front of said pupil center point.

9. The method according to claim 8, further including the step of marking said lens element where said imaginary observance line intersects said lens element.

10. A measurement instrument for recording the height of a pupil center of a person in relation to a point on a set of eyeglasses being worn by that person, said measurement instrument comprising:
    a chassis that selectively attaches to said eyeglasses;
    a swing assembly pivotably coupled to said chassis, wherein said swing assembly swings freely in a vertical plane;
    at least two alignment points supported by said swing assembly, wherein gravity causes said alignment pins remain aligned in a horizontal plane as said swing assembly pivots freely in said vertical plane; and
    a brake arm pivotally coupled to said chassis, wherein said brake arm can be selectivity rotated between a locked position that contacts said swing assembly and prevents said swing assembly from moving relative to said chassis and a free position, where said brake arm does not contact said swing assembly.

11. The measuring assembly according to claim 10, further including a magnet for retaining said brake arm in said locked position when rotated into said locked position.

12. The measurement instrument according to claim 10, further including a measurement scale disposed between said chassis and said swing assembly for visually determining said angle of inclination of said at least two alignment points.

13. The measurement instrument according to claim 10, wherein said at least two measurement points are alignment pins that protrude from said swing assembly.

14. The measurement instrument according to claim 10, wherein said alignment pins are colored in contrast.

* * * * *